US006584345B2

(12) United States Patent
Govari

(10) Patent No.: US 6,584,345 B2
(45) Date of Patent: Jun. 24, 2003

(54) APPARATUS AND METHOD FOR MEASURING A PLURALITY OF ELECTRICAL SIGNALS FROM THE BODY OF A PATIENT

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 298 days.

(21) Appl. No.: 09/805,093

(22) Filed: Mar. 13, 2001

(65) Prior Publication Data

US 2002/0161306 A1 Oct. 31, 2002

(51) Int. Cl.⁷ .................................. A61B 5/04
(52) U.S. Cl. ....................... 600/509; 128/901
(58) Field of Search ............... 324/76.11, 76.29, 324/76.31, 76.33, 130; 600/372–374, 377, 381, 508–509, 515, 546–548, 554; 607/1–2, 115, 116, 119, 122, 123; 702/64

(56) References Cited

U.S. PATENT DOCUMENTS

| 4,649,924 A | | 3/1987 | Taccardi |
| 4,840,182 A | * | 6/1989 | Carlson ..................... 600/507 |

(List continued on next page.)

FOREIGN PATENT DOCUMENTS

| EP | 0900547 A1 | 4/1998 |
| EP | 09900548 A1 | 4/1998 |
| WO | WO96/05768 A1 | 2/1996 |
| WO | WO98/43530 A1 | 10/1998 |
| WO | WO99/06112 A1 | 2/1999 |

OTHER PUBLICATIONS

U.S. patent application Ser. No. 09/122,137, Riesfeld et al.
U.S. patent application Ser. No. 09/357,559, Riesfeld et al.
U.S. patent application Ser. No. 09/506,766, Ben–Haim et al.
U.S. patent application Ser. No. 09/598,862, Govari.

(List continued on next page.)

Primary Examiner—Kennedy Schaetzle
Assistant Examiner—Kristen Droesch
(74) Attorney, Agent, or Firm—Louis J. Capezzuto; Frederick L. Herman

(57) ABSTRACT

An apparatus for measuring electrical signals emanating from a body of a patient, and, in particular, from the patient's heart, comprises a catheter having an electrode array, preferably on its distal end. The apparatus of the invention further comprises a first amplifier for measuring a voltage from a first electrode of the array, and a cascade of differential amplifiers, each of which measures a voltage difference between two successive electrodes in the array. The voltage, $V_n$, at electrode n is given by the expression:

$$V_n = a_1 + \sum_{i=2}^{n} a_i,$$

wherein $a_1$, is the voltage at the first electrode as measured by the first amplifier and each $a_i$, is a differential voltage between electrode i and electrode (i–1) of the array as measured by the differential amplifiers. The catheter electrode array preferably comprises at least one contact electrode and a plurality of non-contact electrodes, the first amplifier is preferably used to measure the signal at the contact electrode and the amplifier cascade is preferably used to measure the signals from the non-contact electrodes. The catheter further preferably comprises at least one position sensor, preferably, an electromagnetic position sensor.

20 Claims, 5 Drawing Sheets

U.S. PATENT DOCUMENTS

| | | | |
|---|---|---|---|
| 4,911,174 A | | 3/1990 | Pederson et al. |
| 5,265,602 A | | 11/1993 | Anderson et al. |
| 5,297,549 A | | 3/1994 | Beatty et al. |
| 5,311,866 A | | 5/1994 | Kagan et al. |
| 5,331,966 A | | 7/1994 | Bennett et al. |
| 5,341,807 A | * | 8/1994 | Nardella ............... 600/381 |
| 5,385,146 A | | 1/1995 | Goldreyer |
| 5,391,199 A | | 2/1995 | Ben-Haim |
| 5,450,846 A | | 9/1995 | Goldreyer |
| 5,487,391 A | | 1/1996 | Panescu |
| 5,546,951 A | | 8/1996 | Ben-Haim |
| 5,579,764 A | * | 12/1996 | Goldreyer ............... 600/374 |
| 5,662,108 A | | 9/1997 | Budd et al. |
| 5,676,153 A | | 10/1997 | Smith et al. |
| 5,704,351 A | * | 1/1998 | Mortara et al. ............ 600/382 |
| 5,738,096 A | | 4/1998 | Ben-Haim |
| 5,820,560 A | * | 10/1998 | Sinderby et al. ........... 600/546 |
| 5,848,972 A | | 12/1998 | Triedman et al. |
| 5,913,820 A | | 6/1999 | Bladen et al. |
| 5,938,603 A | | 8/1999 | Ponzi |
| 5,964,757 A | | 10/1999 | Ponzi |
| 6,050,267 A | * | 4/2000 | Nardella et al. ............ 128/899 |
| 6,259,938 B1 | * | 7/2001 | Zarychta et al. ............ 600/380 |
| 6,381,493 B1 | * | 4/2002 | Stadler et al. ............... 607/9 |
| 6,400,981 B1 | * | 6/2002 | Govari ...................... 600/509 |

OTHER PUBLICATIONS

U.S. patent application Ser. No. 08/793,371, Ben–Haim et al.

European Patent Office Search Report, dated Jun. 12, 2002 for EPO Appln. No. EP 02251741 which relates to U.S. Patent No. 09/805,093, filed Mar. 13, 2001.

* cited by examiner

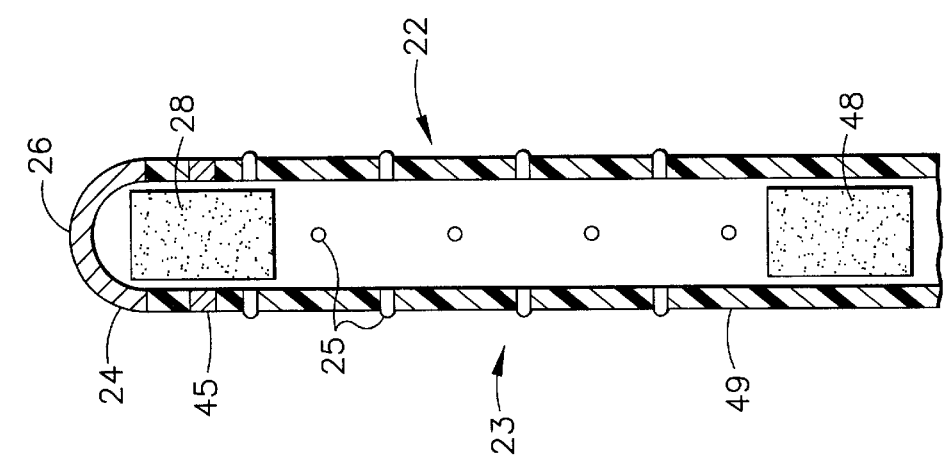
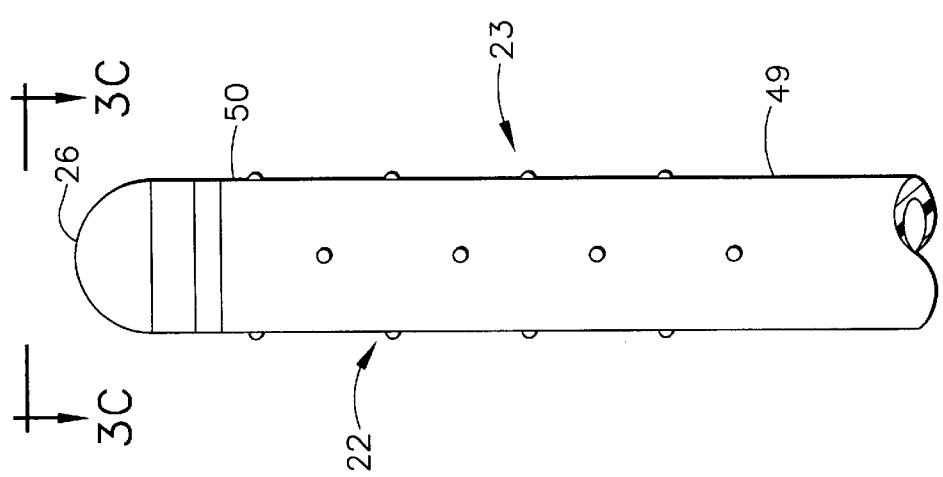
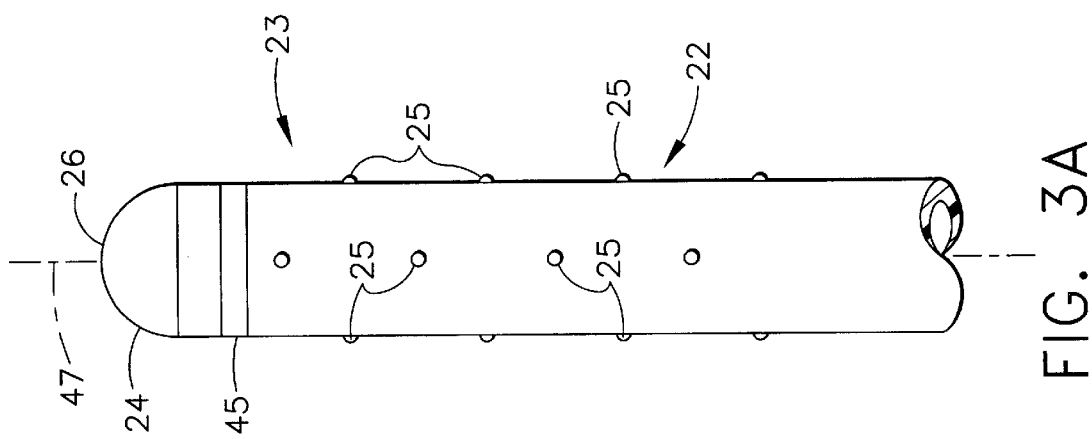

APPARATUS AND METHOD FOR MEASURING A PLURALITY OF ELECTRICAL SIGNALS FROM THE BODY OF A PATIENT

FIELD OF THE INVENTION

This invention is directed to apparatus and methods for measuring a plurality of electrical signals from an electrode array preferably situated in the body of a patient, and is especially suited for measuring a plurality of weak electrical signals emanating from a patient's heart using intracardiac non-contact electrodes.

BACKGROUND OF THE INVENTION

Cardiac arrhythmias, the most common of which is ventricular tachycardia (VT), are a leading cause of death. In a majority of patients, VT originates from a 1 mm to 2 mm lesion located close to the inner surface of the heart chamber. One of the treatments for VT comprises mapping the electrical pathways of the heart to locate the lesion followed by ablation of the active site.

Commonly assigned U.S. Pat. No. 5,546,951; and PCT application WO 96/05768 and its corresponding U.S. patent application Ser. No. 08/793,371 filed on May 14, 1997, all of which are incorporated herein in their entirety by reference, disclose methods for sensing an electrical property of heart tissue, for example, local activation time, as a function of the precise location within the heart. The data are acquired with one or more catheters having electrical and location sensors in their distal tips that are advanced into the heart. Electrical signals are generally acquired with an electrode located at the catheter distal tip after determining that the tip is in stable and steady contact with the endocardium. Methods of creating a map of the electrical activity of the heart based on these data are disclosed in commonly assigned U.S. patent application Ser. Nos. 09/122,137 and 09/357,559 filed on Jul. 24, 1998 and Jul. 22, 1999, respectively, which are also incorporated herein in their entirety by reference. As indicated in these applications, location and electrical activity is preferably initially measured at about 10 to about 20 points on the interior surface of the heart. These data points are then generally sufficient to generate a preliminary reconstruction or map of the cardiac surface to a satisfactory quality. The preliminary map is often combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096 which is incorporated herein in its entirety by reference, maps depicting such motion characteristics may be constructed when the trajectory information is sampled at a sufficient number of points in the heart.

A drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity at multiple points in the heart chamber. Cardiac electrical activity data has been acquired with multi-electrode catheters using contact as well as non-contact methods.

U.S. Pat. No. 5,487,391, directed to systems and methods for deriving and displaying the propagation velocities of electrical events in the heart, is illustrative of contact methods found in the art. In the system disclosed in the '391 patent, the electrical probe is a three-dimensional structure that takes the form of a basket. In the embodiment illustrated in the '391 patent, the basket is composed of 8 splines, each of which carries eight electrodes, for a total of 64 electrodes in the probe. The basket structure is designed such that when deployed, its electrodes are held in intimate contact against the endocardial surface. A problem with the catheters disclosed in the '391 patent is that they are both difficult and expensive to produce. The large number of electrodes in such catheters is also very demanding of the data recording and processing subsystem. There are additional complexities associated with the deployment and withdrawal of these catheters, and increased danger of blood coagulation.

U.S. Pat. No. 5,848,972 to Triedman et al. discloses a method for endocardial activation mapping using a multi-electrode catheter. In the method of the '972 patent, a multi-electrode catheter, preferably, a 50-electrode Webster-Jenkins™ basket catheter from Cordis-Webster of Baldwin Park, Calif., is advanced into a chamber of the heart. Anteroposterior (AP) and lateral fluorograms are obtained to establish the position and orientation of each of the electrodes. Electrograms are recorded from each of the electrodes in contact with the cardiac surface relative to a temporal reference such as the onset of the P-wave in sinus rhythm from a body surface ECG. Interestingly, Triedman et al. differentiate between those electrodes that register electrical activity and those that do not due to absence of close proximity to the endocardial wall. After the initial electrograms are recorded, the catheter is repositioned, and fluorograms and electrograms are once again recorded. An electrical map is then constructed from the above information.

U.S. Pat. No. 4,649,924 to Taccardi discloses a method for the detection of intracardiac electrical potential fields. The '924 patent is illustrative of the non-contact methods that have been proposed to simultaneously acquire a large amount of cardiac electrical information. In the method of the '924 patent, a catheter having a distal end portion is provided with a series of sensor electrodes distributed over its surface. The electrodes are connected to insulated electrical conductors for connection to signal sensing and processing means. The size and shape of the catheter distal end portion are such that the electrodes are spaced substantially away from the wall of the cardiac chamber. The electrodes are preferably distributed on a series of circumferences lying in planes spaced from each other and perpendicular to the major axis of the end portion of the catheter. At least two additional electrodes are provided adjacent the ends of the major axis of the end portion. The '924 patent discloses a single exemplary embodiment in which the catheter comprises eight electrodes spaced equiangularly on each of four circumferences. Thus, in that exemplary embodiment, the catheter comprises 34 electrodes (32 circumferential and two end electrodes). The method of the '924 patent is said to detect the intracardiac potential fields in only a single cardiac beat.

PCT application WO 99/06112 to Rudy, the disclosure of which is incorporated herein by reference, discloses an electrophysiological cardiac mapping system and method based on a non-contact, non-expanded multi-electrode catheter. Electrograms are obtained with catheters having from 42 to 122 electrodes. In addition to the above-described problem of complexity of multi-electrode catheters, the Rudy method requires prior knowledge of the relative geometry of the probe and the endocardium, which must be obtained via an independent imaging modality such as transesophogeal echocardiography. In the Rudy method, after the independent imaging, non-contact electrodes are used to measure cardiac surface potentials and construct maps therefrom.

U.S. Pat. No. 5,297,549 to Beatty et al., the disclosure of which is incorporated herein by reference, discloses a method and apparatus for mapping the electrical potential distribution of a heart chamber. In the Beatty method, an intra-cardiac multielectrode mapping catheter assembly is inserted into the heart. The mapping catheter assembly includes a multi-electrode array with an integral reference electrode, or, preferably, a companion reference catheter. In use, the electrodes are deployed in the form of a substantially spherical array. The electrode array is spatially referenced to a point on the endocardial surface by the reference electrode or by the reference catheter which is brought into contact with the endocardial surface. The preferred electrode array catheter is said to carry at least 24 individual electrode sites.

U.S. Pat. No. 5,311,866 to Kagan et al. discloses a heart mapping catheter assembly including an electrode array defining a number of electrode sites. The mapping catheter assembly also comprises a lumen to accept a reference catheter having a distal tip electrode assembly which may be used to probe the heart wall. In the preferred construction, the mapping catheter comprises a braid of insulated wires, preferably having 24 to 64 wires in the braid, each of which are used to form electrode sites. The catheter is said to be readily positionable in a heart to acquire electrical activity information from a first set of non-contact electrode sites and/or a second set of in-contact electrode sites.

U.S. Pat. Nos. 5,385,146 and 5,450,846 to Goldreyer disclose a catheter that is said to be useful for mapping electrophysiological activity within the heart. The catheter body has a distal tip which is adapted for delivery of a stimulating pulse for pacing the heart or an ablative electrode for ablating tissue in contact with the tip. The catheter further comprises at least one pair of orthogonal electrodes. The orthogonal electrodes are coupled in a pair-wise fashion to differential amplifiers to generate difference signals said to be indicative of the local cardiac electrical activity adjacent the orthogonal electrodes.

U.S. Pat. No. 5,662,108 to Budd et al. discloses a process for measuring electrophysiological data in a heart chamber. The method involves, in part, positioning a set of active and passive electrodes into the heart, supplying current to the active electrodes to generate an electric field in the heart chamber, and measuring the resultant electric field at the passive electrode sites. In one of the disclosed embodiments, the passive electrodes are contained in an array positioned on an inflatable balloon of a balloon catheter. In preferred embodiments, the array is said to have from 60 to 64 electrodes.

Commonly assigned U.S. patent application Ser. No. 09/506,766 filed on Feb. 18, 2000, the disclosure of which is incorporated herein by reference, discloses a novel apparatus and method for rapidly generating an electrical map of a chamber of a heart. In one embodiment, the apparatus and method of the '766 application utilize a catheter including a contact electrode positioned at the catheter distal tip and an array of non-contact electrodes, preferably comprising from about 12 to about 32 electrodes, positioned proximal from the catheter distal tip. The catheter further includes at least one and preferably two location sensors. The catheter is used for rapidly generating an electrical map of the heart within at least one cardiac cycle and preferably includes cardiac ablation and post-ablation validation.

Multi-electrode methods to acquire cardiac electrical signals offer the potential for reducing the time required to generate an electrical map, especially relative to single point contact measurements. A problem with non-contact methods, however, is the weakness of the electrical signal compared to contact measurements, particularly as the electrodes become further removed from the endocardium. Frequently, the magnitude of a non-contact signal is only slightly greater than the noise level. Thus, it is often difficult to accurately discriminate the electrical potential at adjacent electrodes, and this has negative implications on the accuracy of the cardiac map produced from such measurements. Thus, there exists a need for more accurate measurements of weak electrical signals, particularly of the type and of the magnitude encountered in non-contact intracardiac measurements.

SUMMARY OF THE INVENTION

One aspect of the invention is directed to an apparatus for measuring a plurality of electrical signals from an electrode array. The apparatus of the invention comprises a first amplifier for measuring a voltage at a first electrode of the array. The apparatus further comprises a cascade of differential amplifiers, each of which measures an analog voltage difference between two successive electrodes in said array. The voltage, $V_n$, at electrode n is given by the expression:

$$V_n = a_1 + \sum_{i=2}^{n} a_i,$$

wherein $a_1$, is the voltage at the first electrode as measured by the first amplifier and each $a_i$ is a differential voltage between electrode i and electrode (i−1) of the array as measured by the differential amplifiers.

In some embodiments, the apparatus of the invention further comprises a computing processor to compute the voltages at the electrodes.

Another aspect of the invention is directed to an apparatus for measuring electrical signals emanating from a body of a patient. The apparatus comprises a catheter which comprises an electrode array, preferably on its distal end. The apparatus of the invention further comprises a first amplifier for measuring a voltage from a first electrode of the array, and a cascade of differential amplifiers, each of which measures a voltage difference between two successive electrodes in the array. The voltage, $V_n$, at electrode n is given by the expression:

$$V_n = a_1 + \sum_{i=2}^{n} a_i,$$

wherein $a_1$, is the voltage at the first electrode as measured by the first amplifier and each $a_i$, is a differential voltage between electrode i and electrode (i−1) of the array as measured by the differential amplifiers.

In some embodiments, the apparatus of the invention further comprises a computing processor to compute the voltages at the electrodes.

In some embodiments, the catheter electrode array comprises at least one contact electrode and a plurality of non-contact electrodes. In such embodiments, the first amplifier is preferably used to measure the signal at the contact electrode.

In some embodiments, the catheter used in the apparatus of the invention further comprises at least one position sensor. In some embodiments, the catheter comprises a first position sensor proximate the catheter distal tip and a second position sensor proximal to the electrode array. The at least one position sensor is preferably selected from acoustic sensors, magnetic sensors, electromagnetic sensors or combinations thereof. At least one of the position sensors is preferably an electromagnetic position sensor.

Another aspect of the invention is directed to a method for measuring a plurality of electrical signals from an electrode array. The method of the invention comprises providing a first amplifier for measuring a voltage at a first electrode of the array and a cascade of differential amplifiers, each of which measures a voltage difference between two successive electrodes in the array. The method further comprises computing a voltage at each of the electrodes, wherein the voltage, $V_n$, at electrode n is given by the expression:

$$V_n = a_1 + \sum_{i=2}^{n} a_i;$$

wherein $a_1$ is the voltage at the first electrode as measured by the first amplifier and each $a_i$ is a differential voltage between electrode i and electrode (i-1) of the array as measured by the differential amplifiers. The method is preferably employed to measure a plurality of electrical signals emanating from a body of a patient, and more preferably, from a patient's heart.

In some embodiments, the method of the invention further comprises the steps of providing a catheter having an electrode array positioned at its distal end, and advancing the catheter distal end into the patient's heart.

In some embodiments, the electrical signals measured by the method of the invention are used to determine an electrical characteristic of the patient's tissue, such as the peak voltage or the local activation time of cardiac tissue of the patient's heart. The method of the invention further optionally comprises generating a map of the electrical characteristic of a patient's tissue. The method of the invention may further comprise diagnosing a disease state of the tissue from the map of the electrical characteristic, and it may also further comprise treating the tissue.

The present invention will be more fully understood from the following detailed description of the preferred embodiments thereof, taken together with the drawings in which:

BRIEF DESCRIPTION OF THE DRAWINGS

FIG. 3A shows one embodiment of a distal end of a catheter which is included in some embodiments of the apparatus of the invention;

FIG. 3B shows another view of the catheter of FIG. 3B;

FIG. 3C shows the catheter of FIG. 3A and FIG. 3B in longitudinal cross-section;

DETAILED DESCRIPTION OF THE PREFERRED EMBODIMENTS

In one embodiment, the apparatus and method of the invention are directed to measuring a plurality of electrical signals from an electrode array. In preferred embodiments, the electrode array is located on a catheter and is used to measure electrical signals emanating from the body, and particularly, from the heart of a patient.

Figure 1:
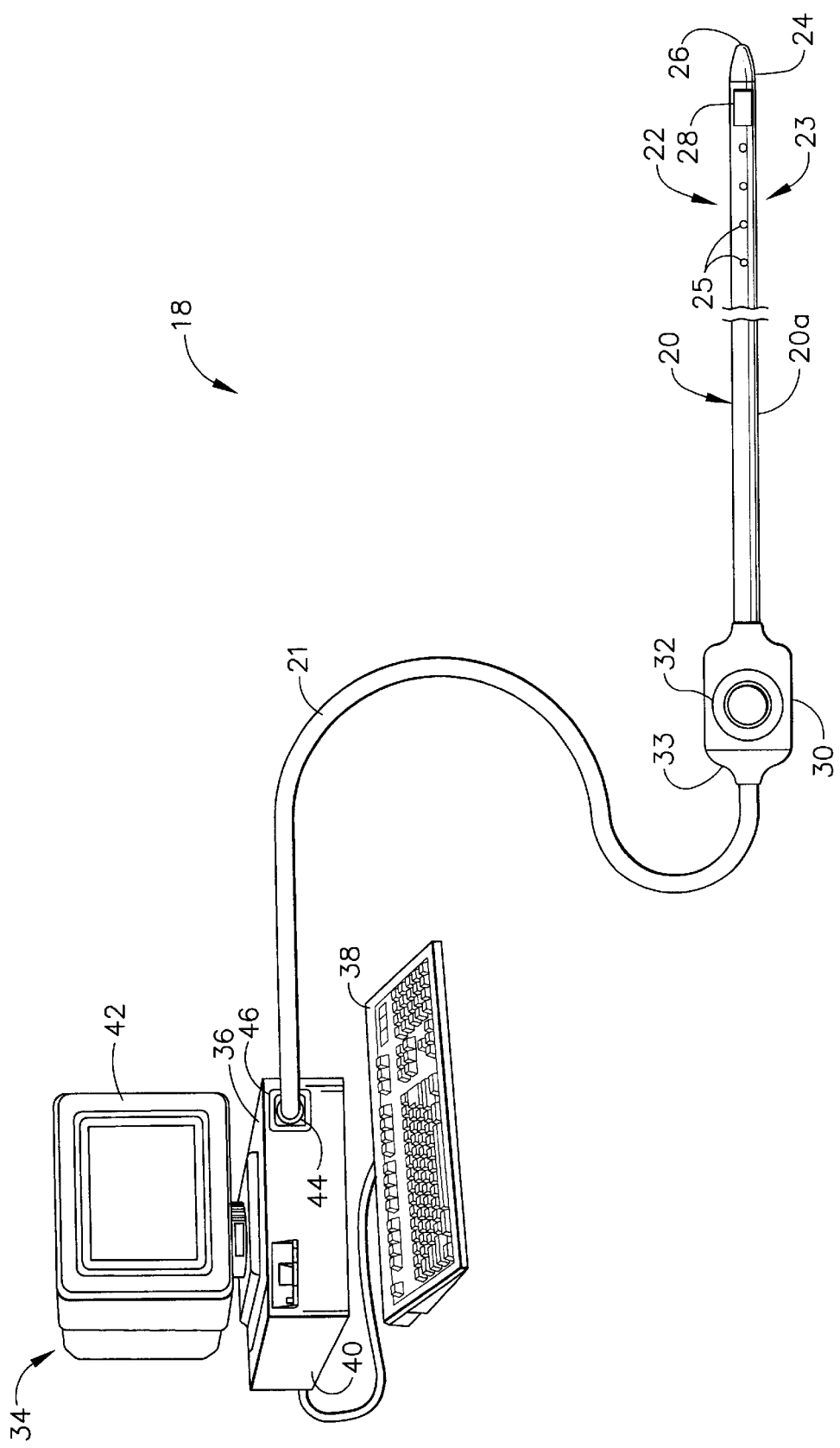
FIG. 1 is a schematic drawing of selected elements of a cardiac electrophysiology system that comprises the apparatus of the invention.
Figure 2:
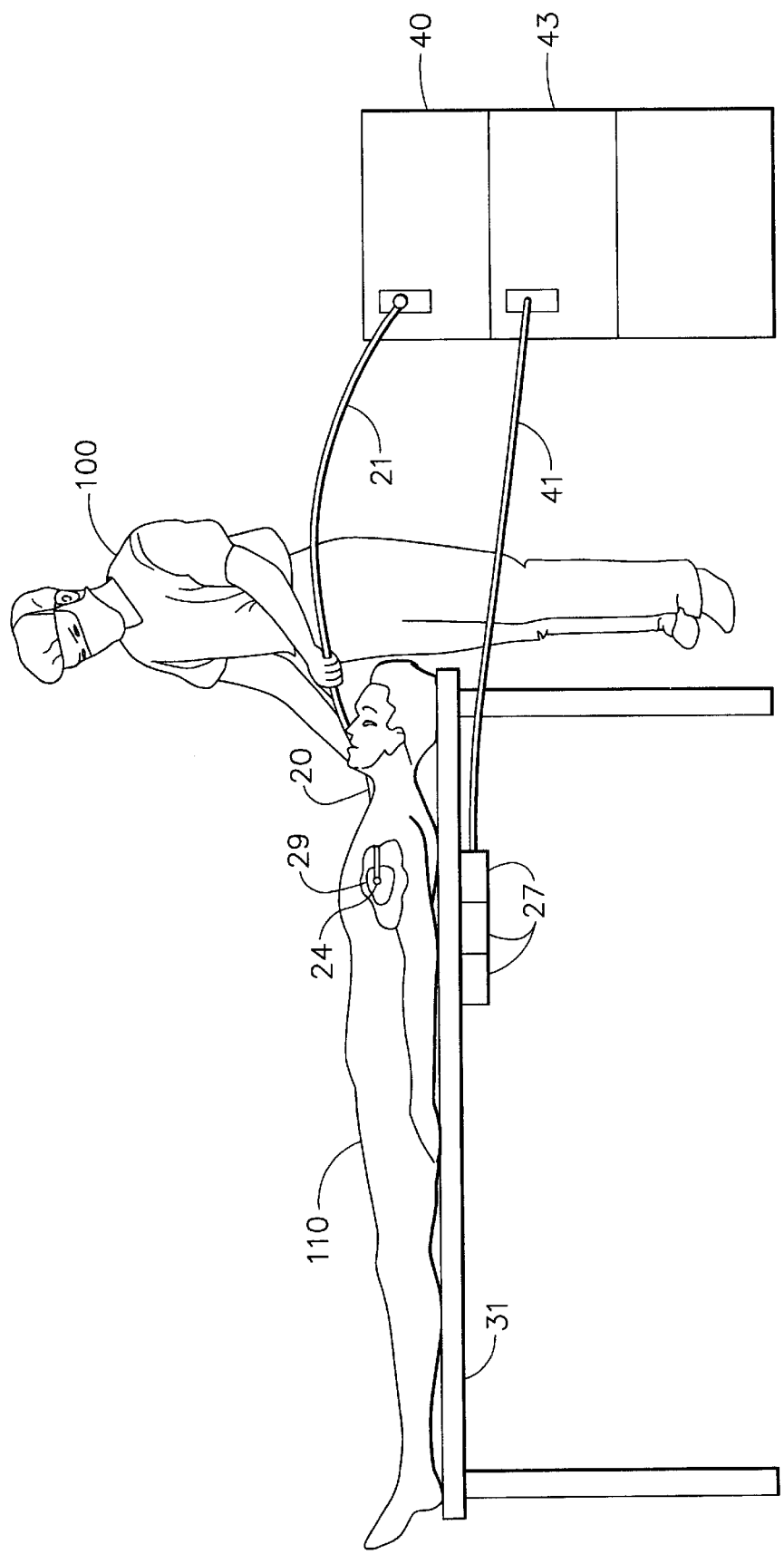
FIG. 2 shows additional elements of the cardiac electrophysiology system of FIG. 1.

A system for measuring the electrical activity in a heart using a catheter-based electrode array is shown in FIGS. 1 and 2. The system, generally designated 18, as best shown in FIG. 1, comprises a diagnostic mapping and therapeutic delivery catheter 20 for insertion into the human body, and preferably, into a chamber of a human heart 29 (FIG. 2). The catheter 20 includes a catheter body 20a having a distal end 22. The distal end 22 includes an electrode 24 at distal tip 26 for contacting and measuring the electrical properties of heart tissue. Electrode 24 is also useful for sending electrical signals to the heart for diagnostic purposes, e.g., for pace mapping, and/or for therapeutic purposes, e.g., for ablating defective cardiac tissue. Distal end 22 of catheter 20 further includes non-contact electrodes 25 for measuring far field electrical signals in the heart chamber. The non-contact electrodes 25 are linearly arranged parallel to the longitudinal axis 47 (FIG. 3A) of the catheter distal end 22. Tip electrode 24, together with non-contact electrodes 25, comprise electrode array 23. Distal end 22 of catheter 20 further includes at least one location sensor 28 that generates signals used to determine the position and orientation of the catheter within the body. Location sensor 28 is preferably adjacent to distal tip 26 of catheter 20. There is, preferably, a fixed positional and orientational relationship of location sensor 28, tip 26 and electrode 24.

Catheter 20 preferably includes a handle 30, which includes controls 32 to steer the distal end 22 of the catheter 20 in a desired direction, such as deflecting the distal end 22, or to position and/or orient it as desired.

The system 18 as shown in FIG. 1 further comprises a console 34, which enables the user to observe and regulate the functions of catheter 20. Console 34 preferably includes a computer 36 which functions as a signal processor, keyboard 38, signal processing circuits 40 which are typically inside the computer 36, and display 42. Signal processing circuits 40 typically receive, amplify, filter and digitize signals from catheter 20, including signals generated by location sensor 28, tip electrode 24 and non-contact electrodes 25 whereupon these digitized signals are used by computer 36 to compute the position and/or the orientation of the catheter as well as the electrical characteristics of the heart chamber. Alternatively, appropriate circuitry may be associated with the catheter 20 itself so that computer 36 receives signals that are already amplified, filtered and/or digitized.

Catheter 20 is coupled to computer 36 via an extension cable 21, which, at its proximal end, comprises a connector 44 adapted to fit in a mating receptacle 46 on console 34. The distal end of cable 21 comprises a receptacle 33 which connects to catheter handle 30. Receptacle 33 is preferably configured to receive catheters of a specific model, and preferably includes user-evident identification of the specific model. One of the advantages in using cable 21 is the ability to connect different models and types of catheters, such as those catheters having different handle configurations, to the same console 34. Different cables 21 can be used to connect a large variety of catheters to console 34. Another advantage in having a separate cable 21 is the fact that the cable 21 does not come into contact with patients. It is, therefore, possible to re-use the cable 21 without sterilization.

Cable 21 further contains one or more isolation transformers (not shown in the figures), which electrically isolate catheter 20 from console 34. The isolation transformers are preferably contained in receptacle 33. Alternatively, isolation transformers may be contained in the associated system electronics.

Additional components used in system 18 with catheter 20 of the present invention are illustrated schematically in FIG. 2. A physician 100 inserts catheter 20 through an incision in the vasculature, i.e., using an intravascular approach, into a chamber of a heart 29 of a patient 110, so that location sensor 28 and electrode array 23, comprising distal tip electrode 24 and non-contact electrodes 25, are inside the chamber. In accordance with an exemplary location sensor described in PCT patent application No. WO 96/05768, in its associated U.S. patent application Ser. No. 08/793,371 filed on May 14, 1997 and in U.S. Pat. No. 5,391,199, which are assigned to the assignee of the present application and whose disclosures are incorporated herein by reference, sensor 28 generates signals in response to externally applied magnetic fields generated by electromagnetic field generator coils 27 which are located near the patient 110 such as fixed to operating table 31. The magnitude of the signals generated by sensor 28 depends on the position and orientation of the sensor in the applied magnetic field. Field generator coils 27 are connected via cable 41 to driver circuits 43. Circuits 43 are connected to computer 36 (FIG. 1), which controls the operation of the generating coils. Alternatively, the system of the invention may employ field generator coils in the catheter and sensors external to the patient.

While the catheter used in some embodiments of the method and apparatus of the invention are described herein with reference to electromagnetic sensors, any other location sensor that provides three-dimensional position information and, optionally, orientation information, may be used in the practice of the invention. Illustrative sensors that are also useful include acoustic sensors and magnetic sensors.

Preferably, measurements by location sensor 28 are substantially synchronized with the heart cycle, so that the resultant maps of electrical activity of the heart chamber depict the chamber geometry at a single point in the heart cycle. Preferably, the maps depict the heart 29 at the end-diastole point in the heart cycle. Synchronization of the locations to a point in the cardiac cycle eliminates errors that may otherwise arise in determining positions of contact electrode 24 and non-contact electrodes 25 due to movement of the heart 29.

FIG. 3A is a plan view of the distal end of one preferred embodiment of a catheter used in the apparatus and method of the invention. FIG. 3B depicts the catheter of FIG. 3A rotated by 90° about its longitudinal axis 47. FIG. 3C depicts the catheter of FIG. 3B in longitudinal cross-section along line 3C—3C. As shown in FIG. 3A, the catheter comprises tip electrode 24 and ring electrode 45. Together, these two electrodes function as a bipolar contact electrode. Non-contact electrodes 25 are arranged in an array that has a proximal end 49 and a distal end 50. The catheter comprises a plurality of non-contact electrodes 25, for instance, sixteen point electrodes 25. Each electrode 25 is circular in cross-section and has a diameter of 1 mm. The non-contact electrodes 25 in array 23 are arranged in four columns spaced circumferentially around the catheter distal end 22 in 90° increments. The location of the electrodes 25 in each column is longitudinally offset relative to the location of the corresponding electrodes in adjacent columns. This arrangement of non-contact electrodes 25 in array 23 allows the non-contact electrodes 25 to simultaneously receive far-field electrical signals from all walls of the chamber in which the catheter 20 is advanced. The catheter 20 further comprises two location sensors 28 and 48 wherein sensor 28 is at the catheter distal tip and sensor 48 is near the proximal end 49 of array 23. Not shown in FIG. 3C are wires that connect each of the sensors 28 and 48 and each of the electrodes 24, 25 and 45 to handle 30, from which signals are transmitted via cable 21 to circuits 40. Likewise not shown is a deflection mechanism which permits deflection of the catheter tip via control 32 on catheter handle 30. The specific design of the catheter deflection mechanism is not critical to the invention, and may be any of the designs for catheter deflection mechanisms known in the art. Catheter steering/deflection mechanisms are disclosed, for example, in U.S. Pat. Nos. 5,964,757; 5,897,529; and 5,938,603; in EP Patent Applications EP 0900547 and EP 0900548, and in PCT Patent Application WO 98/43530, the disclosures of which are hereby incorporated in their entirety by reference.

Figure 4:
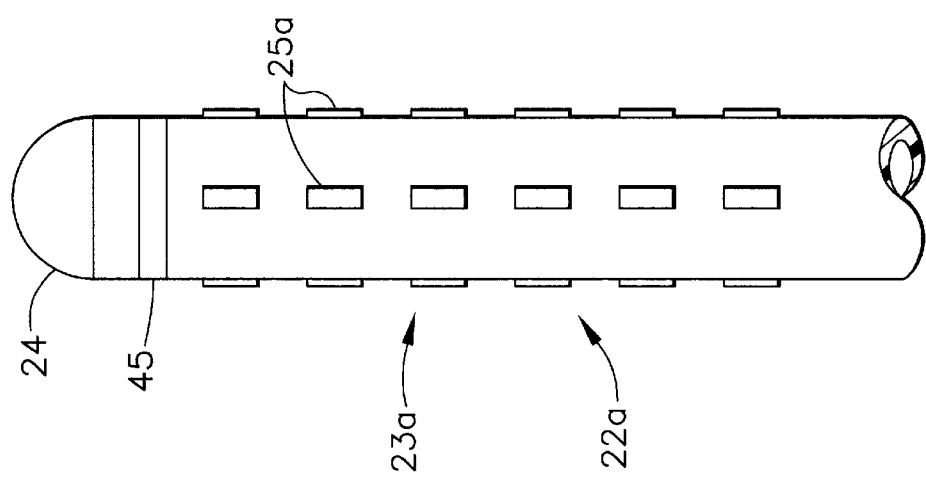
FIG. 4 shows the distal end of another embodiment of a catheter which is included in some embodiments of the apparatus of the invention.

FIG. 4 shows an alternate embodiment of a distal end 22a of a catheter 20a useful in the apparatus and method of the invention. The catheter 20a consists of tip electrode 24 and ring electrode 45. A total of twenty-four non-contact electrodes 25a arranged in four columns of six electrodes each and spaced circumferentially at 90° increments about the catheter distal end 22a. In the embodiment shown in FIG. 4, the non-contact electrodes 25a are rectangular in shape, having dimensions of 1 mm×3 mm, and are spaced within a column at a distance of 8 mm between centers. The catheter distal end 22a of FIG. 4 likewise contains two location sensors (not shown), one at the catheter tip 26 and the other at the proximal end of electrode array 23a.

Electrode array 23a preferably comprises from about twelve to about thirty-two non-contact electrodes 25a. More preferably, array 23a comprises from about sixteen to about twenty-four non-contact electrodes 25a. In one preferred embodiment, array 23a comprises less than twenty non-contact electrodes 25a.

Figure 5:
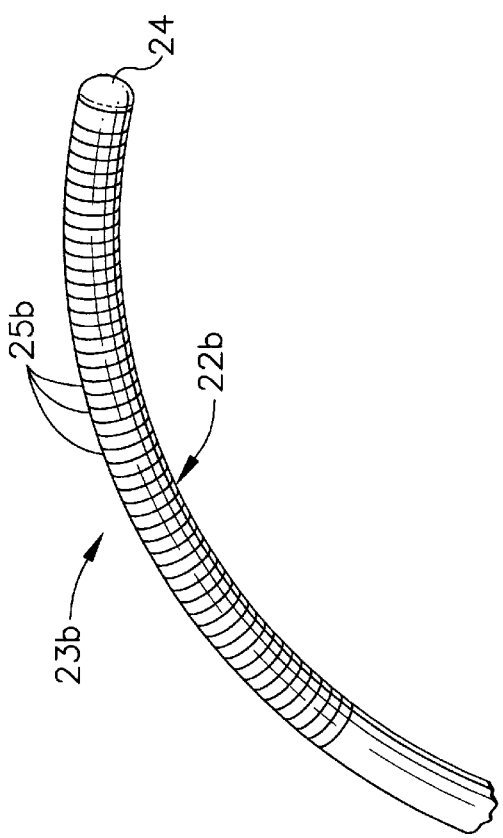
FIG. 5 shows a distal end of a third embodiment of a catheter which is included in some embodiments of the apparatus of the invention.

As shown in FIGS. 3A, 3B, 3C and 4, non-contact electrodes 25 and 25a in electrode arrays 23 and 23a are discontinuous about the circumference of catheter distal ends 22 and 22a, respectively. FIG. 5 is a schematic, pictorial illustration showing a distal portion 22b of another preferred catheter 20b that is useful in the apparatus and method of the present invention. The catheter 20b of FIG. 5 is substantially similar in construction and use to catheter 20 and 20a, described in detail hereinabove, except that instead of point electrodes 25 or rectangular plaques 25a, catheter 20b comprises a plurality of ring electrodes 25b. The ring electrode 25b closest to tip electrode 24 may be used in conjunction with tip electrode 24 to measure bipolar potentials at the cardiac surface. In one exemplary embodiment, the catheter has thirty-two ring electrodes, spaced approximately 0.5 mm apart.

While the catheter distal ends 22 and 22a shown in FIGS. 3A, 3B, 3C, 4 and 5 have bipolar distal tip contact electrodes, it will be understood that catheter distal ends containing unipolar distal tip electrodes are also considered to be useful in practicing the method and apparatus of the present invention.

In practicing some embodiments of the method of the invention, it is desirable to know the position and orientation of each of the non-contact electrodes 25, 25a and 25b contained in array 23, 23a and 23b of catheter 20, 20a and 20b, respectively. In order to know the location and orientation of each of the electrodes, the catheter used in the method and apparatus of the invention preferably employs two or more location sensors such as sensors 28 and 48 as shown in FIG. 3C. One of these sensors is preferably placed in the catheter distal tip 26 while a second sensor is preferably placed at the proximal end 49 of electrode array 23. Preferably, at least one of these location sensors provides six degrees of location and orientation information, i.e., three position coordinates (x, y and z) and the three orientation coordinates (pitch, roll and yaw). A suitable, location sensor 28 and 48 that provides six degrees of location information is described, for example in PCT application WO 96/05768 and in its corresponding U.S. patent application Ser. No. 08/793,371, the disclosure of which is incorporated herein by reference.

Knowing the three-dimensional position and orientation of each of the sensors and the geometry of the electrodes 25 at the catheter distal end 22, the position and orientation of each of the electrodes 25 may be calculated, for example, using spline techniques.

Under suitable circumstances, e.g., knowledge of the stiffness characteristics of the catheter, other image information, and the use of stiff, short non-contact electrode arrays, it may be possible to use a catheter having only a single position sensor in the practice of the method of the invention. In such cases, the sensor is preferably located at the catheter distal tip 26.

In catheters having multiple location sensors, not all sensors need to provide six degrees of location information. For example, as shown in FIG. 3C, sensor 28 preferably senses and transmits signals indicative of six degrees of location information. While sensor 48 may be a six-degree sensor, a sensor providing less than six degrees of location information may also be used. For example, a sensor which senses five degrees of location information (three position coordinates, pitch and yaw) is described in U.S. Pat. No. 5,913,820, the disclosure of which is incorporated herein by reference. Such sensors may be used as the second sensor proximate the proximate end 49 of electrode array 23. Alternatively, a plurality of location sensors, each providing less than six degrees of location information, may be used. For example, three or more location sensors, each providing three degrees of location information, may be used to define the location of all points on the catheter.

The catheter used in the apparatus and method of the invention preferably has a diameter between about 5 French and about 11 French (3 French=1 mm). More preferably, the catheter of the invention has a diameter between about 6 French and about 8 French.

In conventional prior art systems that measure electrical potentials from multiple electrodes, the signal from each electrode is typically fed to an individual, independent amplifier where the instantaneous voltage is measured. The signals from each electrode are typically measured against a reference such as the right leg body surface electrode or against Wilson's central terminal (WCT), which is a composite signal based on right arm, left arm and left leg body surface signals. Alternatively, the signal from each electrode is measured against ground. In any event, in the case of multiple electrodes, each signal is typically measured in parallel from its own amplifier against a common reference or ground. This scheme works well in the case of contact electrodes, where the amplitude of the signal generated at each electrode is far in excess of the noise threshold. In the case of non-contact electrodes, particularly where the electrodes are closely spaced and are removed from contact with the endocardium, the difference in readings from two adjacent electrodes may be of the same order of magnitude as the noise level of the measurement instrumentation. For example, for electrodes that are spaced two mm apart and that are positioned between about one to about two centimeters from the endocardium, the difference between the signals at each of the electrodes may be only of the order of about 10 to about 50 microvolts, which is of the same order of magnitude as the noise level of the instrumentation, which is of the order of about 20 to about 40 microvolts. The apparatus and method of the invention permit the accurate discrimination of these signals.

Figure 6:
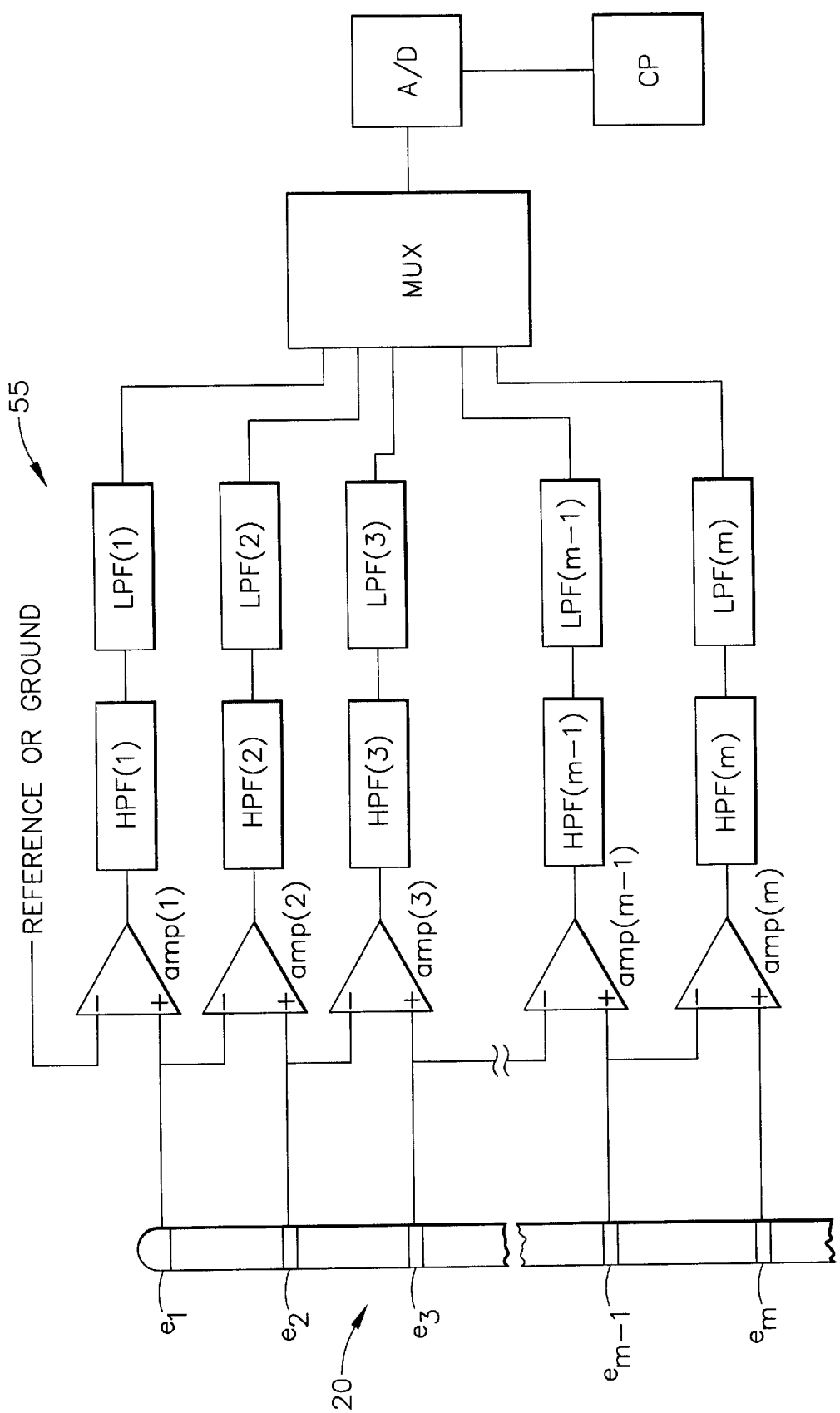
FIG. 6 shows signal processing circuit, components of which are included in the apparatus of the invention.

A portion of the signal processing circuits 40 used in the apparatus of the invention for measuring signals from an array of electrodes is shown in FIG. 6. As shown in FIG. 6, the apparatus collects signals from multi-electrode catheter 20 containing an array of a total of m electrodes. The apparatus of the invention comprises a total of m amplifiers, labeled amp(1) through amp(m) in FIG. 6, wherein the number of amplifiers corresponds to the number of electrodes in the electrode array. Amplifiers amp(2) through amp(m) comprise a cascade of differential amplifiers, wherein each amplifier in the cascade measures a differential voltage between its corresponding electrode and the previous electrode in the electrode array. For example, amplifier 3, amp(3), measures the differential voltage of electrode 3 $e_3$ and electrode 2 $e_2$.

The catheter electrodes are connected to the amplifiers by wires that are internal to the catheter that connect each of the electrodes to a terminal in the catheter handle 30. From the handle, the circuit to the amplifiers is completed by cable 21 which connects the terminal in catheter handle 30 with signal processing circuits 40.

Distal end portion 22 of catheter 20 of FIG. 6 contains one tip electrode labeled $e_1$ and a plurality of ring electrodes labeled $e_2$ through $e_m$. The signal from tip electrode $e_1$ is measured by amplifier amp(1), either relative to one of the reference signals enumerated above or relative to ground. The output of amp(1), $a_1$, is thus a direct measure of $V_1$, the potential at electrode $e_1$.

$$a_1 = V_1$$

Differential amplifier amp(2), the first member of the amplifier cascade, measures the voltage difference $a_2$ between electrode $e_2$ and electrode $e_1$.

$$a_2 = V_2 - V_1$$

Rearranging and substituting for $V_1$, the potential $V_2$ at electrode $e_2$ is given by the expression:

$$V_2 = a_1 + a_2$$

Differential amplifier amp(m-1) is the penultimate amplifier in the cascade, and measures the differential signal between electrodes $e_{m-1}$ and $e_{m-2}$. Finally, amplifier amp(m) measures the differential signal between electrodes $e_m$ and $e_{m-1}$.

By analogy to the above equations for the potential at electrode $e_2$, it may be shown that the potential, $V_n$, of any electrode $e_n$ of the electrode array may be given by the expression:

$$V_n = a_1 + \sum_{i=2}^{n} a_i,$$

wherein $a_1$ is the potential at the first electrode as measured by the first amplifier, and each of the $a_i$ is a differential voltage between electrode i and electrode (i−1) of the array as measured by the respective differential amplifiers.

As further illustrated in FIG. 6, signal processing circuits 40 typically further include filters to filter the signals output by each of the amplifiers. Typically, the signals are filtered with both high pass filters (labeled HPF(1) through HPF(M)) and low pass filters (labeled LPF(1) through LPF(M)). The signals are then fed to a multiplexer (MUX) from which they are then digitized by an A/D converter (A/D). The digitized electrode signals are then transmitted to other portions of signal processing circuits for further processing. For example, the digitized signals are sent to a computing processor for computation of the potentials of the individual electrodes in the array.

The benefits expected to be associated with the apparatus and method of the invention include improved signal-to-noise ratio for weak signals, especially from non-contact electrodes positioned remotely from the endocardial surface. Additional benefits include the ability to regain the single electrode potentials from the differential measurements as described herein.

Co-pending, commonly assigned U.S. patent application Ser. No. 09/506,766 filed on Feb. 18, 2000 and Ser. No. 09/598,862 filed on Jun. 21, 2000, the disclosures of which are incorporated herein by reference, disclose methods of mapping the electrical activity of the heart. Using the methods disclosed therein, the electrical potentials sensed at the non-contact electrodes 25 of catheter 20 may be used to compute potentials at the endocardial surface. These endocardial potentials may be used to reconstruct local endocardial electrograms, or to determine an electrical characteristic of the cardiac tissue such as the peak voltage or the local activation time (LAT). The LAT is typically determined as a characteristic of the local electrogram, such as the time of maximum depolarization of the tissue. LAT is also usually referenced in time relative to a reference event such as a particular feature of the body-surface electrogram. The resultant electrical characteristic of the cardiac tissue may be plotted as a function of the cardiac geometry to generate a map of the characteristic.

Using methods disclosed in U.S. patent application Ser. No. 09/122,137 filed on Jul. 24, 1998 and in U.S. patent application Ser. No. 09/357,559 filed on Jul. 22, 1999, the disclosures of which are incorporated herein by reference, the data on cardiac geometry collected from the location sensors 28 and 48 and the electrical characteristics of the cardiac tissue as described herein may be used to generate a three dimensional reconstruction of the electrical activity of the cardiac chamber. These reconstructions are very useful for identifying aberrant electrical pathways that are responsible for potentially life threatening conditions such as ventricular tachycardia. Having identified an aberrant pathway from the reconstruction, the catheter used in the method and apparatus of the invention may be further used to deliver treatment to the tissue, as, for example, ablation of the tissue with energy supplied to the tissue via contact electrode 24.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An apparatus for measuring a plurality of electrical signals from an electrode array, said apparatus comprising:
 a first amplifier for measuring a voltage at a first electrode of said array; and
 a cascade of differential amplifiers, each of said differential amplifiers of said cascade measuring a voltage difference between two successive electrodes in said array;
 wherein the voltage, $V_n$, at electrode n is given by the expression $$V_n = a_1 + \sum_{i=2}^{n} a_i,$$

wherein $a_1$ is the voltage at said first electrode as measured by said first amplifier and each of said $a_i$ is a differential voltage between electrode i and electrode (i−1) of said array as measured by said differential amplifiers.

2. Apparatus according to claim 1 which further comprises a computing processor to compute said voltages at said electrodes.

3. An apparatus for measuring electrical signals emanating from a body of a patient, said apparatus comprising:
 a catheter comprising an electrode array;
 a first amplifier for measuring a voltage from a first electrode of said array; and
 a cascade of differential amplifiers, each of said differential amplifiers of said cascade measuring a voltage difference between two successive electrodes in said array;
 wherein the voltage, $V_n$, at electrode n is given by the expression $$V_n = a_1 + \sum_{i=2}^{n} a_i,$$

wherein $a_1$ is the voltage at said first electrode as measured by said first amplifier and each of said $a_i$ is a differential voltage between electrode i and electrode (i−1) of said array as measured by said differential amplifiers.

4. Apparatus according to claim 3 which further comprises a computing processor to compute said voltages at said electrodes.

5. Apparatus according to claim 3 wherein said electrode array comprises at least one contact electrode and a plurality of non-contact electrodes.

6. Apparatus according to claim 5 wherein said first amplifier is used to measure the signal at said contact electrode.

7. Apparatus according to claim 3 wherein said catheter further comprises at least one position sensor.

8. Apparatus according to claim 7 wherein said catheter comprises a first position sensor proximate the catheter distal tip and a second position sensor proximal to the electrode array.

9. Apparatus according to claim 7 wherein said at least one position sensor is selected from acoustic sensors, magnetic sensors, electromagnetic sensors or combinations thereof.

10. Apparatus according to claim 9 wherein at least one of said at least one position sensors is an electromagnetic position sensor.

11. A method for measuring a plurality of electrical signals from an electrode array, said method comprising:
providing:
a first amplifier for measuring a voltage at a first electrode of said array; and
a cascade of differential amplifiers, each of said differential amplifiers of said cascade measuring a voltage difference between two successive electrodes in said array; and
computing a voltage at each of said electrodes, wherein the voltage, $V_n$, at electrode n is given by the expression $$V_n = a_1 + \sum_{i=2}^{n} a_i;$$

wherein $a_1$ is the voltage at said first electrode as measured by said first amplifier and each of said $a_i$ is a differential voltage between electrode i and electrode (i−1) of said array as measured by said differential amplifiers.

12. A method according to claim 11 wherein said plurality of electrical signals emanate from a body of a patient.

13. A method according to claim 12 wherein said plurality of electrical signals emanate from a patient's heart.

14. A method according to claim 13 which further comprises the steps of:

providing a catheter having a distal end, said electrode array positioned at said catheter distal end; and advancing said catheter distal end into said patient's heart.

15. A method according to claim 14 wherein said measured electrical signals are used to determine the local activation time of cardiac tissue of said patient's heart.

16. The method according to claim 14 which further comprises generating a map of an electrical characteristic of cardiac tissue of said patient's heart.

17. The method of claim 16 wherein said electrical characteristic is the peak voltage of said cardiac tissue.

18. The method of claim 16 wherein said electrical characteristic is the local activation time of said cardiac tissue.

19. The method of claim 16 which further comprises diagnosing a disease state of said cardiac tissue from said map.

20. The method of claim 19 which further comprises treating said cardiac tissue.

* * * * *